United States Patent [19]

Foos

[11] Patent Number: 5,221,007
[45] Date of Patent: Jun. 22, 1993

[54] TELESCOPING CAPSULE PACKAGE FOR SUPORTING FRAGILE ARTICLE

[75] Inventor: Douglas E. Foos, Barrington Hills, Ill.

[73] Assignee: Plastofilm Industries Inc., Wheaton, Ill.

[21] Appl. No.: 838,554

[22] Filed: Feb. 19, 1992

[51] Int. Cl.⁵ .......................................... B65D 81/08
[52] U.S. Cl. .................... 206/363; 206/523
[58] Field of Search ................ 206/363–365, 206/521, 523, 587, 591, 592, 594; 267/153, 182

[56] References Cited

U.S. PATENT DOCUMENTS

| | | | |
|---|---|---|---|
| 3,434,708 | 3/1969 | Hawk, Jr. | 267/153 |
| 3,460,786 | 8/1969 | Rivin | 267/153 |
| 3,910,410 | 10/1975 | Shaw | 206/471 |
| 4,019,633 | 4/1977 | Roth | 206/471 |
| 4,418,898 | 12/1983 | Atsumi et al. | 267/153 |
| 5,082,112 | 1/1992 | Dunklee | 206/471 |
| 5,105,942 | 4/1992 | van Veen et al. | 206/471 |

FOREIGN PATENT DOCUMENTS

| | | | |
|---|---|---|---|
| 0954050 | 9/1974 | Canada | 206/521 |
| 1398858 | 4/1965 | France | 267/153 |

*Primary Examiner*—Jimmy G. Foster
*Attorney, Agent, or Firm*—Welsh & Katz, Ltd.

[57] ABSTRACT

A telescoping capsule package for supporting a fragile article having a plurality of flexible strands forming a basket. The package includes a first capsule portion having a tubular wall, a closed end and an open end opposite the closed end, a second capsule portion having a tubular wall, a closed end and an open end opposite the closed end, and a biasing device located within the package for biasing the first and second capsule portions axially relative to each other. The second capsule portion is dimensioned so that when the respective open ends of the first and second capsule portions are placed in opposing, engaged relationship to each other to form the package, the second capsule portion telescopes relative to the first telescoping portion.

20 Claims, 1 Drawing Sheet

TELESCOPING CAPSULE PACKAGE FOR SUPORTING FRAGILE ARTICLE

BACKGROUND OF THE INVENTION

The present invention relates generally to specialty packages for protecting fragile articles during shipment, and specifically to such a package used to protect an article having an easily deformable collapsible basket or net-like portion.

Certain fragile articles, such as medically related devices, must be shipped in a specified orientation to minimize damage and to maximize their effectiveness. One such device includes a disposable surgical aid having a basket made of flexible plastic strands. During surgery, the basket is looped around specified body tissues to grasp and move the tissues out of the way of surgical procedures. When such devices are shipped in conventionally available packaging formats, including but not limited to thermoformed trays, blister and card packages, or foam-padded boxes, it has been found that the fragile baskets collapse or otherwise deform. This deformation impairs the utility of the device, and as such, conventionally available packages are unsuitable for packaging these devices.

Thus, it is an object of the present invention to provide a package for a fragile article which protects the article and maintains it in a specified orientation during shipment and prior to use.

It is another object of the present invention to provide a package for an article having a collapsible basket portion wherein the package supports the basket portion in a desired "inflated" position.

It is yet another object of the present invention to provide a biased package for a fragile article wherein the package expands to support the article in a desired orientation.

SUMMARY OF THE INVENTION

Accordingly, the above-identified objects and advantages are met by the present telescoping capsule package, which is designed to support fragile articles in a desired pre-use position. Articles to be packaged which have a plurality of elongate strand-like members or other collapsible components are, when packaged with the present invention, maintained in an inflated or otherwise supported position.

More specifically, the present invention provides a telescoping capsule package for supporting a fragile article, including a first capsule portion having a tubular wall, a closed end and an open end opposite the closed end, and a second capsule portion having a tubular wall, a closed end and an open end opposite the closed end, the second capsule portion being dimensioned so that when the respective open ends of the first and second capsule portions are placed in opposing, engaged relationship to each other to form the package, the second capsule portion telescopes relative to the first telescoping portion. The invention also includes a biasing device located within the package for biasing the first capsule portion axially relative to the second capsule portion.

In another embodiment, the invention provides a telescoping capsule package for supporting a fragile article having a plurality of flexible, generally longitudinal strands arranged to define a basket. The package includes first and second capsule portions each having a tubular wall, a closed end and an open end opposite the closed end, the second capsule portion being dimensioned so that when the respective open ends of the first and second capsule portions are placed in opposing relationship to each other to form the package, the second capsule portion telescopes relative to the first telescoping portion.

In addition, the wall of the first capsule portion has at least one groove, and the wall of the second capsule portion has at least one groove, the grooves of the first and second capsule portions are disposed to slidingly engage each other, and each groove is configured to support one of the strands of the basket. Also included is a biasing device located within the package for biasing the first and second capsule portions axially relative to each other.

DESCRIPTION OF THE PREFERRED EMBODIMENT

Figure 1:
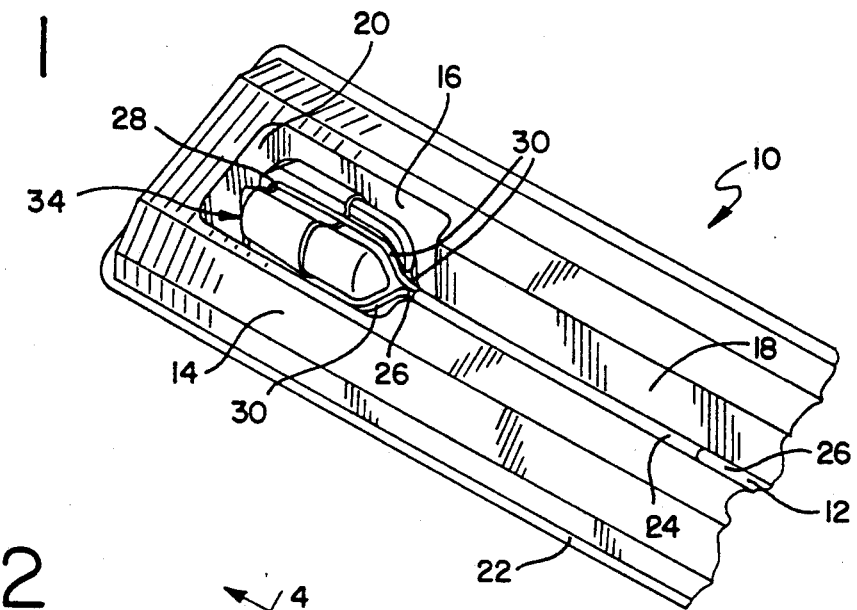
FIG. 1 is a fragmentary top perspective elevational view of a fragile article shown being supported by a telescoping capsule package according to the present invention.

Referring now to the drawing, wherein like numerals indicate like features, FIG. 1 depicts a package, generally designated 10, for a fragile article 12, such as a medically oriented device. The package 10 includes a tray portion 14 which is preferably thermoformed from a thermoplastic material, such as polyethylene, polypropylene, polyvinyl chloride, polystyrene, or the like. At least one article carrying formation 16 is integrally formed into the tray portion 14, and may include an elongate groove 18 configured for carrying elongate items, and a generally box-shaped recess 20 configured for carrying relatively larger articles. The tray portion 14 may also be provided with stabilizing formations 22 depicted as a peripheral lip, which stabilize the package 10 when it is placed on a flat surface. Other types of stabilizing formations 22 as are well known in the art may be included in the configuration of the base portion 14.

Although a variety of fragile articles 12 are contemplated for use with the present invention, in the preferred embodiment the packaged fragile article is a surgical aid including and elongate tubular sleeve 24 through which a control rod 26 is inserted. The control rod 26 is provided with a position locking mechanism (not shown) as is known in the art at one end, and a tissue or organ grasping basket portion 28 at an opposite end. The basket portion 28 includes a plurality of elongate, generally longitudinally arrayed flexible strands 30 which are integral with the control rod 26. The strands 30 are joined at respective ends to form the basket portion 28.

In view of the fact that the basket portion 28 is used to grasp tissues during surgery and move them out of the way of surgical procedures, it is important that the strands 30 maintain their desired shape during packaging, shipment and pre-use handling. Without some support, the strands 30 have a tendency to collapse, thus losing their "inflated" basket shape and impairing their use during surgery.

Figure 2:
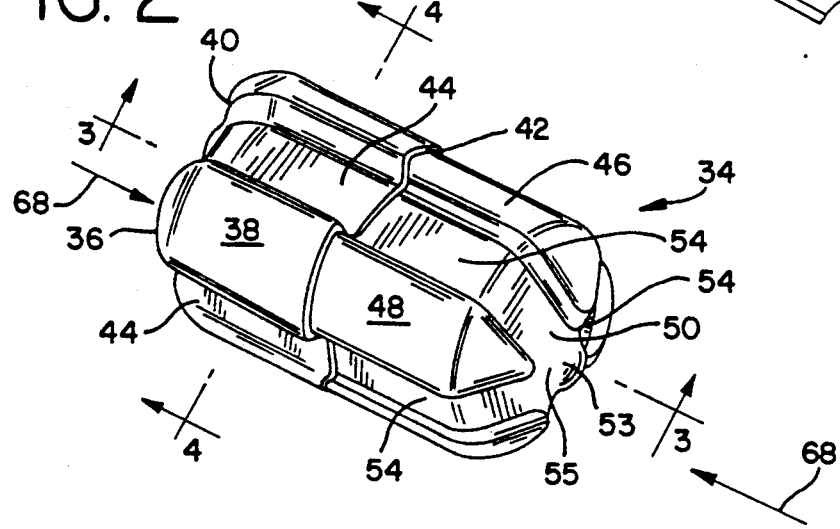
FIG. 2 is a top perspective elevational view of the capsule package of the invention.
Figure 3:
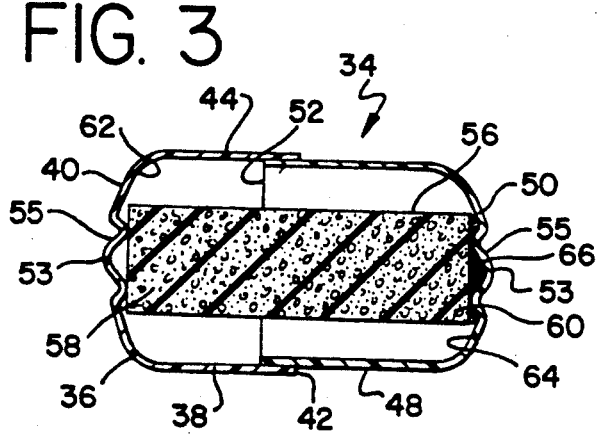
FIG. 3 is a sectional view taken along the line 3-3 of FIG. 2 and in the direction indicated generally.
Figure 4:
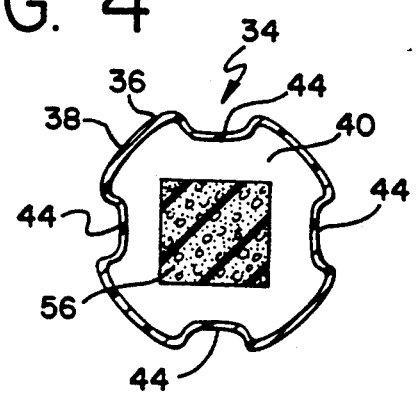
FIG. 4 is a sectional view taken along the line 4—4 of FIG. 2 and in the direction indicated generally.

Referring now to FIGS. 2-4, to maintain the strands 30 of the basket portion 28 in a supported or inflated position, the package 10 is provided with the telescoping capsule package 34 of the invention. The capsule package 34 includes a first capsule portion 36 having a tubular wall 38, a closed end 40 and an open end 42 opposite the closed end. The wall 38 is provided with at least one groove 44 which is generally parallel in orientation relative to the longitudinal axis of the first capsule portion 36.

In the preferred embodiment, there are four grooves 44, each constructed and positioned to correspond to the placement of one of the strands 30 of the basket portion 28.

Also included in the telescoping capsule package 34 is a second capsule portion 46 having a tubular wall 48, a closed end 50 and an open end 52 opposite the closed end. Both the first and second capsule portions 36, 46 are preferably thermoformed out of thermoplastic material which may be similar in composition to the material used in forming the tray portion 14, but may be fabricated from any thermoplastic material being self-supporting, sterilizable, and inexpensive to produce. Also, if desired, the corresponding closed ends 40, 50 may be provided with a pointed formation 53 for more accurately positioning the basket portion 28.

In similar fashion to the first telescoping portion 36, the second telescoping portion 46 has at least one and preferably four grooves 54, which correspond in size and orientation to the grooves 44 in the portion 36. In fact, when the telescoping package 34 is assembled, the grooves 44 and 54 will be in registry with each other. Also, in each of the first and second capsule portions 36, 46, respective first ends 55 of the grooves 44 and 54 meet at a common location on the corresponding closed end 40, 50 of the respective capsule portion.

The second capsule portion 46 is similar in configuration to the first capsule portion 36, with the main distinction that the second portion has a slightly smaller diameter. When opposing open ends 42, 52 of the corresponding first and second capsule portions 36, 46, respectively, are placed in engagement upon assembly of the package 34, a sliding, telescoping engagement results.

To effectively maintain the basket portion 28 in a supported position, the telescoping package 34 is provided with a biasing device 56 which biases the first and second capsule portions 36, 46 axially relative to each other, but does not cause disengagement of the two portions. In the preferred embodiment, the biasing device 56 is an elongate resilient member of a medically acceptable grade of sponge-type polymeric foam, having a first end 58 and a second end 60. The biasing device 56 is depicted as a rectangular block of foam; however other configurations are contemplated, as long as the device is dimensioned to engage respective inside surfaces 62, 64 of the closed ends 40 and 50 when the first and second portions 36, 46 are in their uncompressed position depicted in FIGS. 2 and 3. In addition, other types of biasing devices such as coiled springs, accordion folded members, or the like may be equally suitable, provided they are cost effective and acceptable for packaging medically oriented articles.

To facilitate assembly of the capsule package 34, it is preferred that one of the ends 58, 60 of the biasing device 56 is fastened to the corresponding inside surface 62, 64 of the closed end 40 or 50. Suitable adhesive 66 (best seen in FIG. 3) may be used to fasten the biasing device 56 in this orientation.

Another characteristic of the biasing device 56 is that it have enough resiliency to return the capsule package 34 to the at rest or unloaded position depicted in FIGS. 2 and 3, while not disengaging the first capsule portion 36 from the second capsule portion 46. As seen in FIG. 3, there is sufficient overlap of the respective open ends 42, 52 to prevent disengagement.

In order to hold the basket portion 28 in its desired shape, the capsule package 34 is designed to exert a slight biasing force on the strands 30. This biasing force is generated by designing the capsule package 34 to have a length which is slightly longer than the length of the basket portion 28. The first and second capsule portions 36, 46 are compressed together in the direction indicated by the arrows 68 (best seen in FIG. 2), as by grasping the closed ends 40, 50 to overcome the biasing force of the biasing device 56. While in this compressed condition, the capsule package 34 is placed within the area defined by the strands 30 and released. Upon release, the biasing device 56 causes the first and second capsule portions 36, 46 to be displaced in an axial direction so that a slight stress is placed on the strands 30 to keep the basket portion 28 in an open position. The strands 30 may then be placed in their respective grooves 44, 54 where they are retained until the telescoping capsule package 34 is removed. The package 34, and the basket portion 28, are then placed in the box-shaped recess 20 and the remainder of the article 12 is placed in the elongate groove 18.

While a particular embodiment of the telescoping package for supporting fragile articles of the invention has been shown and described, it will be appreciated by those skilled in the art that changes and modifications may be made thereto without departing from the invention in its broader aspects and as set forth in the following claims.

What is claimed is:

1. A telescoping capsule package for supporting a fragile article, comprising:
   a first capsule portion having a tubular wall, a closed end and an open end opposite said closed end;
   a second capsule portion having a tubular wall, a closed end and an open end opposite said closed end, said second capsule portion being dimensioned so that when said respective open ends of said first and second capsule portions are placed in opposing, engaged relationship to each other to form said package, said second capsule portion telescopes relative to said first capsule portion;
   said wall of said first capsule portion has at least one groove, and said wall of said second capsule portion has at least one groove, said corresponding grooves of said first and second capsule portions being disposed to slidingly engage each other; and
   biasing means being located within said package for biasing said first capsule portion axially relative to said second capsule portion.

2. The package as defined in claim 1 wherein said grooves of said respective first and second capsule portions are substantially parallel with the longitudinal axis of each said capsule portion.

3. The package as defined in claim 2 wherein said corresponding walls of said first and second capsule portions each have four grooves.

4. The package as defined in claim 3 wherein on each of said capsule portions, first ends of said grooves meet at a common location on said closed end of said respective capsule portion.

5. The package as defined in claim 2 wherein said corresponding walls of said first and second capsule portions each have four grooves, and on each of said capsule portions, first ends of said grooves meet at a common location on said closed end of said respective capsule portion and said closed end of each of said capsule portions defines a pointed formation.

6. The package as defined in claim 1 wherein said closed end of each of said capsule portions defines a pointed formation.

7. The package as defined in claim 1 wherein said second capsule portion has a slightly smaller diameter than said first capsule portion so that said open end of second capsule portion slides within said open end of first telescoping portion.

8. The package as defined in claim 1 wherein said biasing means is an elongate resilient member having a first end and a second end, said first and second ends configured so that upon assembly of said package, said first and second ends are located in contacting relationship with corresponding inner surfaces of said closed ends of said first and second capsule portions.

9. The package as defined in claim 8 wherein said biasing means is made of resilient polymeric foam.

10. The package as defined in claim 8 wherein said first end of said biasing means is fastened to said corresponding inner surface of said closed end of said respective capsule portion to which said biasing means is engaged.

11. The package as defined in claim 1 wherein said biasing means is configured so that upon the release of a longitudinal compressive force exerted on said package, said biasing means returns said capsule portions to an unloaded position wherein said first and second capsule portions are maintained at a specified position relative to each other.

12. A telescoping capsule package for supporting a fragile article, comprising:
 a first capsule portion having a tubular wall, a closed end and an open end opposite said closed end;
 a second capsule portion having a tubular wall, a closed end and an open end opposite said closed end, said second capsule portion being dimensioned so that when said respective open ends of said first and second capsule portions are placed in opposing, engaged relationship to each other to form said package, said second capsule portion telescopes within said first telescoping portion; and
 biasing means including an elongate resilient member with first and second ends configured so that upon assembly of said package, said first and second ends are located in contacting relationship with corresponding inner surfaces of said closed ends of said first and second capsule portions, said resilient member being fastened at at least one of said first and second ends to an inner surface of one of said closed ends of said first and second capsule portions, and upon assembly of said package, said resilient member being configured to engage said opposite closed end of said package for biasing said first and second capsule portions axially relative to and apart from each other, while not separating said capsule portions from each other.

13. The package as defined in claim 12 wherein said wall of said first capsule portion has at least one groove, and said wall of said second capsule portions at least one groove, said corresponding grooves of said first and second capsule portions being disposed to slidingly engage each other.

14. The package as defined in claim 13 wherein said grooves of said respective first and second capsule portions are substantially parallel with the longitudinal axis of each said capsule portion.

15. The package as defined in claim 12 wherein said biasing means is made of resilient polymeric foam.

16. A telescoping capsule package for supporting a fragile article having a plurality of flexible, generally longitudinal strands arranged to define a basket, comprising:
 a first capsule portion having a tubular wall, a closed end and an open end opposite said closed end;
 a second capsule portion having a tubular wall, a closed end and an open end opposite said closed end, said second capsule portion being dimensioned so that when said respective open ends of said first and second capsule portions are placed in opposing, engaged relationship to each other to form said package, said second capsule portion telescopes relative to said first telescoping portion;
 said wall of said first capsule portion has at least one groove, and said wall of said second capsule portion has at least one groove, said grooves of said first and second capsule portions being disposed to slidingly engage each other, and each said groove being configured to support one of the strands of the basket; and
 biasing means being located within said package for biasing said first and second capsule portions axially relative to each other.

17. The package as defined in claim 16 wherein said grooves of said respective first and second capsule portions are substantially parallel with the longitudinal axis of each said capsule portion.

18. The package as defined in claim 16 wherein the basket has four strands and said corresponding walls of said first and second capsule portions each have four grooves.

19. The package as defined in claim 16 wherein on each of said capsule portions, first ends of said grooves meet at a common location on said closed end of said respective capsule portion, and said closed end of each of said capsule portions defines a pointed formation.

20. A telescoping capsule package for supporting a fragile article having a plurality of flexible, generally longitudinally arranged strands arranged to define a basket, comprising:
 a first capsule portion having a tubular wall, a closed end and an open end opposite said closed end;
 a second capsule portion having a tubular wall, a closed end and an open end opposite said closed end, said second capsule portion being dimensioned so that when said respective open ends of said first and second capsule portions are placed in opposing, engaged relationship to each other to form said package, said second capsule portion telescopes relative to said first capsule portion; and
 biasing means being located within said package for biasing said first capsule portion axially relative to said second capsule portion, said biasing means providing a specified degree of axial biasing force to exert a slight stress on the strands of the basket arrayed around said telescoping first and second capsule portions to maintain the basket in an open, supported position.

* * * * *